United States Patent [19]
Orange et al.

[11] Patent Number: 5,817,038
[45] Date of Patent: Oct. 6, 1998

[54] WATERPROOF COVERING AND EQUIPMENT SUPPORT FOR LIMBS

[76] Inventors: Beatrice Marie Orange, 14701 E. Colfax, Space #D-79, Aurora, Colo. 80011; David L. Boardman, 3015 S. Garfield St., Denver, Colo. 80210

[21] Appl. No.: 294,064

[22] Filed: Aug. 22, 1994

[51] Int. Cl.⁶ ........................................... A61F 5/00
[52] U.S. Cl. ................... 602/3; 602/62; 602/63
[58] Field of Search ................... 602/3, 61–63; 128/849, 852, 855, 856; 604/292, 293, 304, 308

[56] References Cited

U.S. PATENT DOCUMENTS

| | | |
|---|---|---|
| 2,229,575 | 1/1941 | Kaplan . |
| 2,244,871 | 6/1941 | Guinzburg .................. 128/856 X |
| 2,334,206 | 11/1943 | Knohl . |
| 3,657,741 | 4/1972 | Bianco . |
| 3,659,599 | 5/1972 | McLaughlin . |
| 3,741,203 | 6/1973 | Liman . |
| 3,744,491 | 7/1973 | Fischer .................. 604/293 X |
| 3,824,998 | 7/1974 | Snyder . |
| 3,989,040 | 11/1976 | Lofgun et al. ................. 128/856 |
| 4,036,220 | 7/1977 | Bellasalma . |
| 4,139,003 | 2/1979 | Little et al. . |
| 4,308,864 | 1/1982 | Small et al. .................. 128/856 |
| 4,346,699 | 8/1982 | Little et al. . |
| 4,363,317 | 12/1982 | Broucek . |
| 4,423,722 | 1/1984 | Dickman . |
| 4,523,586 | 6/1985 | Couri . |
| 4,562,834 | 1/1986 | Bates et al. . |
| 4,610,245 | 9/1986 | Beiarman . |
| 4,639,945 | 2/1987 | Betz . |
| 4,646,727 | 3/1987 | Chambers . |
| 4,727,864 | 3/1988 | Wiesenthal et al. . |
| 4,911,151 | 3/1990 | Rankin et al. . |
| 4,986,265 | 1/1991 | Caposi . |
| 5,016,648 | 5/1991 | Brown et al. . |
| 5,063,919 | 11/1991 | Silverberg ....................... 602/3 |
| 5,143,762 | 9/1992 | Ho et al. . |

FOREIGN PATENT DOCUMENTS 2630908  11/1989  France ........................... 602/3

Primary Examiner—Linda C. Dvorak
Attorney, Agent, or Firm—Rick Martin

[57] ABSTRACT

A system for supporting and protecting wounds, incisions, transdermal procedural sites, and associated medical equipment from moisture and other contaminants is disclosed. The invention is an assembly of a waterproof outer cover, at least one water absorbent dam, and an equipment support sleeve deployable around a limb or extremity. The waterproof outer cover is a limp tube or sleeve with at least one waterproof closure providing an annular seal around a user's extremity. The water absorbent dam is detachably deployed just inside the seal around the extremity to absorb any moisture which breaches the seal during water exposure and to catch any retained moisture as the waterproof sleeve is removed. The support sleeve secures equipment to the extremity within the waterproof cover.

14 Claims, 3 Drawing Sheets

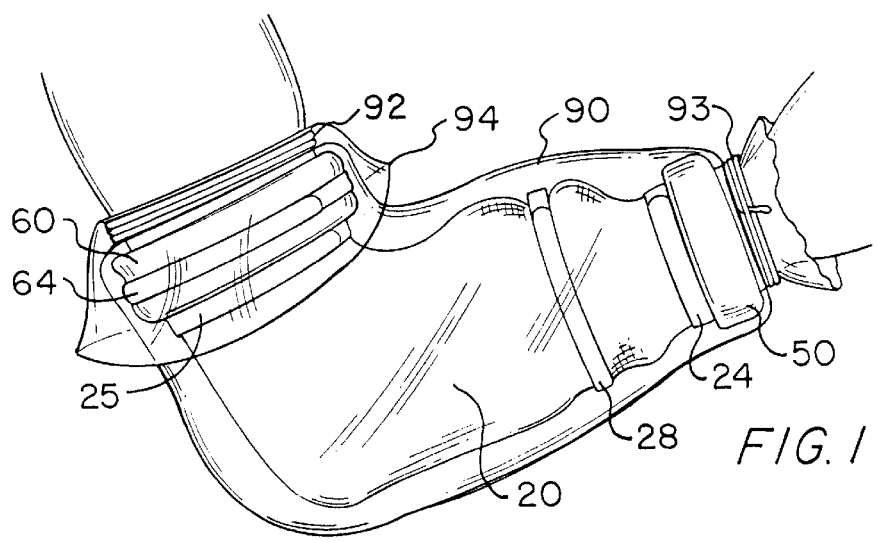
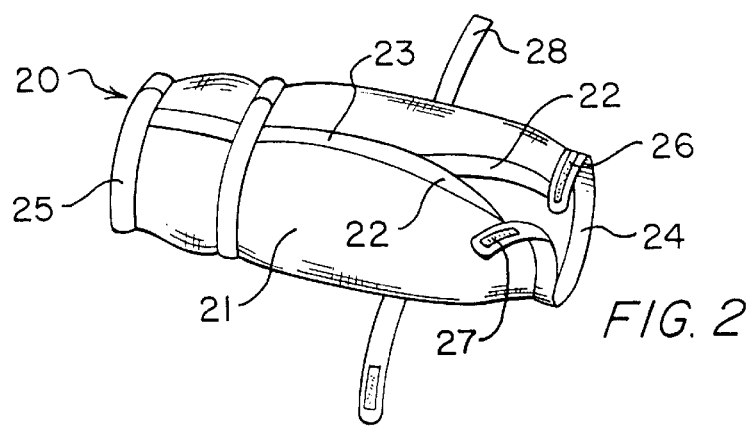
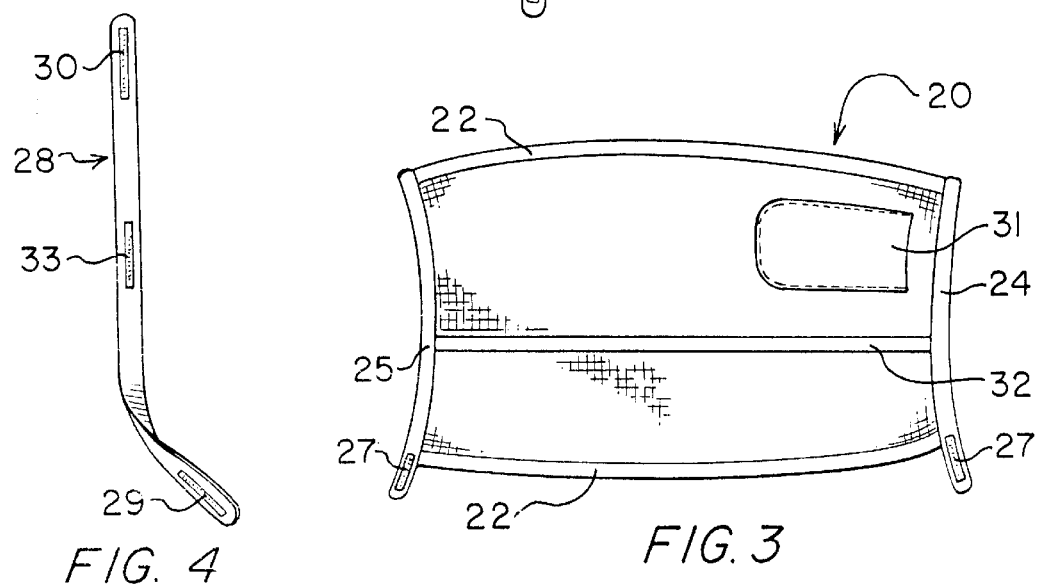

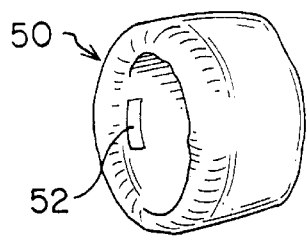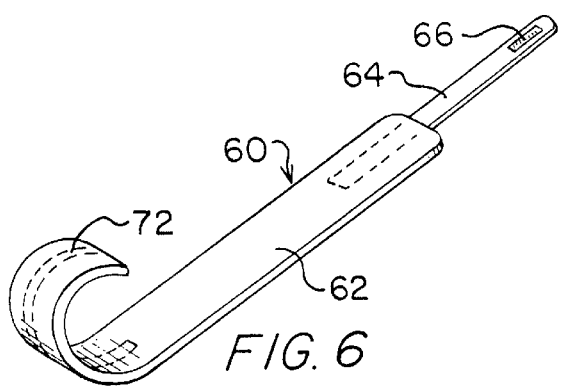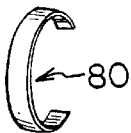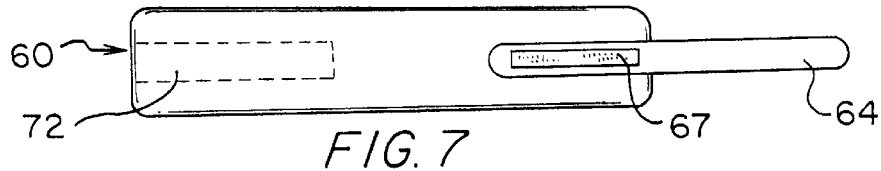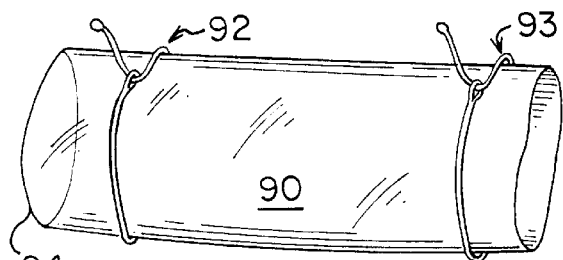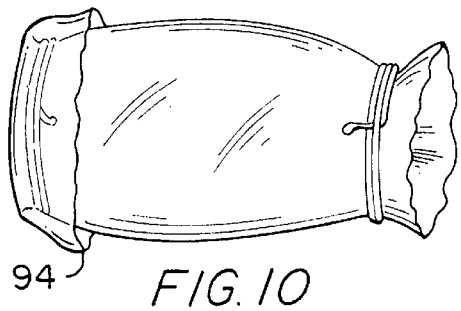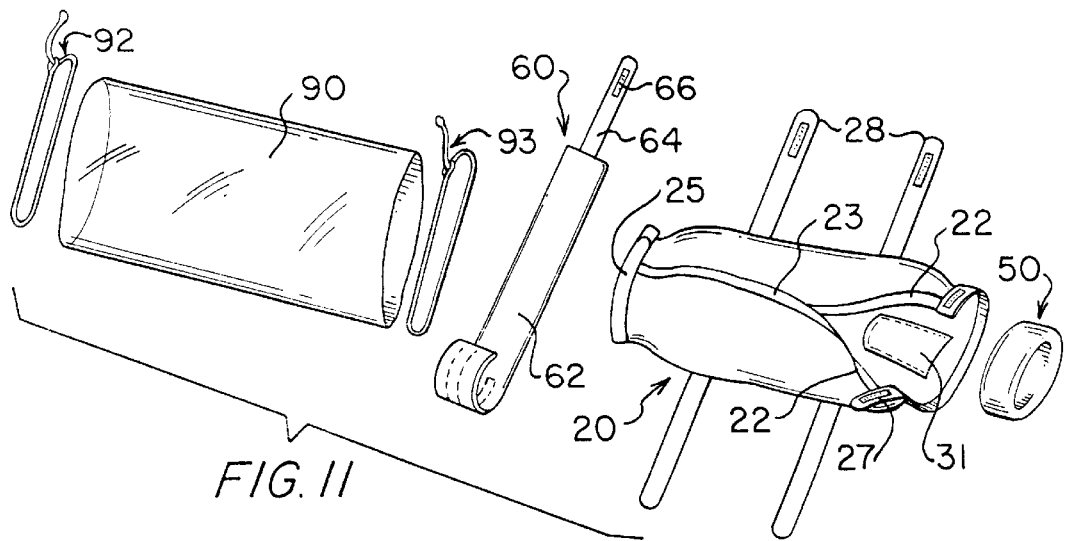

WATERPROOF COVERING AND EQUIPMENT SUPPORT FOR LIMBS

FIELD OF THE INVENTION

The present invention relates to limb coverings. In particular the present invention discloses a medical equipment support sleeve with water absorbent dams inserted within a waterproof limb covering.

BACKGROUND OF THE INVENTION

Since the discoveries by Louis Pasteure, the medical art has recognized the need to maintain the cleanliness of skin injuries, and many devices have been produced to help maintain that cleanliness. Any breach of the protective barrier provided by the skin may become a pathway for infection. Therefore, the maintenance of cleanliness and dryness in areas where the skin has been compromised is a primary goal of the healthcare professional. A significant portion of the medical patent literature describes devices designed to maintain medical cleanliness. Unsterile liquids readily contaminate wounds and medical equipment. The medical art recognizes the cost and labor savings provided by effective waterproof shields. There is an increasing trend to move convalescent health care out of hospitals and into the home environment, where able convalescents are trained to maintain the cleanliness of their own skin and equipment. Some of the equipment used at home is expensive and labor intensive. Therefore, reliable, inexpensive waterproof shields for convenient use by patients and healthcare professionals alike are needed.

A broad sector of the pertinent prior art deals with various methods of obtaining a reliable waterproof seal between a waterproof shield and the skin. U.S. Pat. Nos. 4,346,699 (1982) to Little et al., 5,143,762 (1992) to Ho, and 4,639,945 (1987) to Betz disclose elastic shields which tighten elasticly around a limb. Each relies exclusively on the tightness of the seal to exclude water. No provision is made for internal water absorbance or for internal equipment support.

U.S. Pat. Nos. 5,063,919 to Silverberg and 5,016,648 to Brown et al. disclose waterproof covers with exterior constrictive bands that tighten around a waterproof cover and an enclosed limb to form watertight seals. No water absorbent members or internal equipment supports are disclosed.

Support garments such as surgical support stockings are represented in the art by U.S. Pat. No. 2,334,206 (1943) to Knohl. In general, these patents provide means to increase pressure within a limb but are not intended to provide adjustable support of additional equipment. They do not describe waterproof or water absorbent characteristics to protect the injury or equipment.

U.S. Pat. No. 3,741,203 (1973) to Liman discloses a thin spongelike elastomeric foam layer attached to the interior of a waterproof arm cover which acts as an absorbent barrier and as an impediment to water flow. Because of its intimate attachment, the foam layer conforms to the folds of the plastic barrier and collapses under the pressure of the binding tape to form an integral part of the primary seal. The overall absorbent capacity of the foam is quite small. In the event of primary seal failure, the foam provides no further impediment to inflowing water. During removal of the arm cover, the foam comes away with the cover, allowing any residual moisture flow freely into the equipment. No internal equipment support is disclosed.

None of the reviewed patents disclose an integrated system which includes a medical equipment support sleeve inside a waterproof sleeve. Also none of the reviewed prior art discloses the use of detachable water absorbent dams or cuffs deployed within a waterproof sleeve to provide a secondary barrier to the inflow of water. Water adsorbent dams significantly improve the overall reliability of the water barrier. Finally, none of the disclosed prior art discloses an adjustable support to effectively and economically protect medical equipment attached to a limb from moisture when showering, bathing, or washing.

SUMMARY OF THE INVENTION

The main object of this invention is an integrated system of a medical equipment support sleeve inserted in a waterproof sleeve with a secondary absorbent barrier.

Another object of this invention is improving the waterproof seal between a waterproof sleeve and a limb through use of water adsorbent dams or cuffs.

Another object of this invention is an efficient, cost effective means of protecting medical equipment attached to a limb from moisture when bathing or showering.

Other objects of this invention will appear from the following description and appended claims, reference being had to the accompanying drawings forming a part of this specification wherein like reference characters designate corresponding parts in the several views.

The present invention is an assembly of a waterproof outer cover, at least one water absorbent dam, and an equipment support sleeve. The water proof outer cover is a limp waterproof tube or sleeve with at least one waterproof closure providing an annular seal around a user's extremity. The water absorbent dam is detachably deployed just inside the seal around the extremity to absorb any moisture which breaches the seal during water exposure and to catch any retained or remaining moisture as the waterproof sleeve is removed. The support sleeve is designed to secure and bind equipment to the extremity within the waterproof cover.

The support sleeve is designed to provide general constrictive support for perilimb equipment and dressings. The sleeve holds bulky or heavy medical equipment in place and confines tubes, wires, loose ends and tape so as not to interfere with the donning of the waterproof cover. This protects the waterproof cover from internal puncture, minimizes seal displacement and failure due to equipment movement and protects the inner side of the waterproof cover from adhesives and provides an additional barrier to maintain cleanliness. The design further allows variations that promote the free circulation of air and provide visual inspection of the equipment. Adjustable cuffs provide a non-slip engagement around the appendage and have an attachment point for the water absorbent dam. A detachable strap(s) provides additional adjustable circumferential binding for equipment within. The sleeve may provide pockets, pouches, baffles, and access openings as needed.

The water absorbent dam is designed to snugly encircle a limb to provide 360 degree secondary protection from moisture seeping through the seal between a waterproof cover and the skin. Upon removal of a waterproof cover, the dam provides further protection by catching any moisture inadvertently trapped within the folds and creases of a wet cover. The dam can be removably attached to the cuff of a support sleeve and together the dam and cuff will stop the creep of a waterproof cover along the appendage.

The waterproof cover is a loose fitting tubular sleeve designed to slip easily over an appendage encumbered with medical equipment. A waterproof seal between the sleeve and the skin is achieved using an adjustable elastic band placed around the exterior of the sleeve near the sleeve opening. The cover is made with a stretch and tear resistant waterproof material which is thin and limp enough that when compressed by the elastic bands any folds or wrinkles of the gathered waterproof material will collapse and not provide a channel for water flow.

BRIEF DESCRIPTION OF THE DRAWINGS

FIG. 1 is a side view of a mid-limb waterproof support system shown deployed over an elbow and forearm.

FIG. 2 is an oblique side view of a cylindrical support sleeve open at one end.

FIG. 3 is a top view of the inside of a support sleeve.

FIG. 4 is a top view of a detachable support strap.

FIG. 5 is an oblique view of an absorbent dam elastic cuff design.

FIG. 6 is an oblique view of an unwrapped absorbent dam with a "C" shaped internal stay and elastic hook and loop closure band. This view primarily shows the inside (skin side) of the dam.

FIG. 7 is a view of the outside of an unwrapped adsorbent dam with an internal "C" shaped stay and elastic hook and loop closure band.

FIG. 8 is an oblique side view of a "C" shaped internal stay.

FIG. 9 is an oblique side view of a waterproof sleeve with untightened adjustable elastic bands.

FIG. 10 is an oblique side view of a waterproof sleeve with tightened adjustable elastic bands, with the band ends wrapped around and tucked in.

FIG. 11 is an exploded view of the system, including a mid-limb support sleeve, absorbent dams, and a waterproof sleeve with adjusted elastic bands to seal the waterproof sleeve to the skin.

Figure 12:
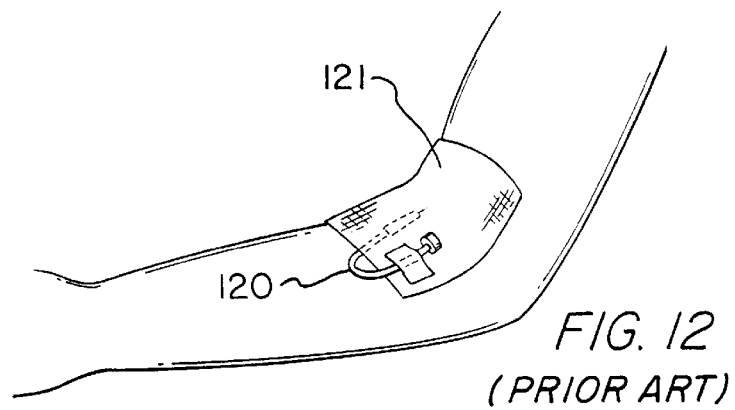
FIG. 12 (prior art) is a perspective view of a forearm having a PICC-line in place.

Before explaining the disclosed embodiment of the present invention in detail, it is to be understood that the invention is not limited in its application to the details of the particular arrangement show, since the invention is capable of other embodiments. Also, the terminology used herein is for the purpose of description and not of limitation.

DETAILED DESCRIPTION OF THE INVENTION

FIG. 1 shows a side view of a mid-arm version of the present invention. For clarity sake, folds, wrinkles, and surface textures in the materials are not shown. The waterproof sleeve 90 is drawn as a very transparent covering to more clearly display the underlying absorbent dams 50, 60 and support sleeve 20. It is understood that though transparent materials may be used for construction of waterproof sleeves 90, the sleeves 90 may also be constructed from more translucent or opaque materials as well.

The support sleeve 20 consists of an elastic mesh tube 21 with integral non-slip cuffs 24, 25 at each end. A single support strap 28 provides additional localized support around the forearm. A water absorbent elastic dam or cuff 50 snugly surrounds the wrist partially covering the support sleeve cuff 24. A second water absorbent dam 60 is wrapped around the upper arm and is secured with an adjustable elastic band 64. A transparent waterproof sleeve 90 encloses the support sleeve 20 and absorbent dams 50, 60. Two adjustable elastic sealing bands 92, 93 wrap around the waterproof sleeve forming waterproof seals with the skin of the upper arm and wrist. The edge of the waterproof sleeve 94 is folded down over the adjustable elastic sealing band 92 around the upper arm so that water will not collect around the upper arm seal.

FIGS. 2, 3, and 4 provide various views of a preferred midarm version of the internal equipment support sleeve. FIG. 2 shows a cylindrical support sleeve 20, the body of which is made of an open elastic mesh 21. Hook and loop tape (for example Velcro®) closures 22 are attached to opposite edges of the mesh 21 to form a separable longitudinal seam 23. Adjustable cuffs 24, 25 fasten to secure the open ends of the sleeve 20 snugly around the extremity. The cuffs 24, 25 are made of slip resistant material, such as rubberized cloth. Hook and loop surfaces 26, 27 on the cuffs provide an adjustable cuff closure as well as attachment points for the adsorbent dams. Support strap(s) 28 provide additional adjustable circumferential binding means.

FIG. 3 depicts the inner surface of the support sleeve 20 as it would look with the hook and loop tape closure 22 unfastened. The adjustable cuffs 24, 25 have non-slip rubberized surfaces. The hook and loop closure surface 27 is attached to the tab end of the cuff. A pocket 31 is attached to the inner surface to provide a secure place for medical equipment. Additional pockets (not shown) attached to the inner surface are of course possible.

FIG. 4 depicts an adjustable elastic support strap 28 with a half twist to exhibit the closure surface. Hook and loop closure surfaces 29, 30 provide adjustable closure means. Hook surface 33 mates with loop surface 32 of FIG. 3 to provide longitudinal adjustment of the support strap 28 on the exterior of the support sleeve 20.

FIG. 5 is a simple elastic absorbent dam or cuff 50 designed to be pulled over a wrist or ankle similar to a tennis wrist band. The interior surface may have a small patch of loop fastener tape 52 attached to secure the water absorbent dam to the mating hook surface 26 of a support cuff 24 of FIG. 2.

FIG. 6 is an oblique view of an unwrapped water absorbent dam 60 primarily showing the inside (skin side) of the dam 60. FIG. 7 is a top view of the outside of an unwrapped water absorbent dam 60. The main body of the dam 60 is a water absorbent pad 62. One end has an oblong pocket 72 into which is inserted a "C" shaped stay 80. An elastic strap 64 with hook and loop closure sites 66, 67 is attached to the other end of the absorbent dam and provides an adjustable 360 degree securement around the water absorbent dam 60 and the limb or extremity.

FIG. 8 shows a "C" shaped stay 80 which is inserted into pocket 72 (see FIGS. 6 and 7). This "C" shaped stay 80 is stiff enough to provide a firm grip around the limb. For example, flexible stiff plastic would be appropriate for "C" shaped stay construction.

FIG. 9 and 10 show a transparent waterproof tube 90. FIG. 9 shows the waterproof tube 90 with untightened adjustable elastic sealing bands 92, 93. FIG. 10 shows the same waterproof tube with bands 92, 93 tightened. In FIG. 10, the long end of each tightened sealing band is wrapped around the waterproof tube 90 and the extremity and tucked under itself. This creates a watertight closure between the waterproof tube and the skin of the user. One or both of the ends of the waterproof tube 94 may be turned over the sealing bands 92, 93 if the ends 94 beyond the elastic closure on the extremity are prone to catch water.

FIG. 11 shows an axially exploded drawing of a mid-arm waterproof support system of FIG. 1. The user would place his arm on an open support sleeve 20, put any loose medical equipment into pocket 31, and close the sleeve around his arm by engaging hook and loop tapes 22 (such as Velcro®) forming a longitudinal seam 23. This forms a cylindrical sleeve around the arm. The support cuffs 24, 25 would then be secured snugly around the wrist and upper arm by engaging the hook and loop fasteners on the ends of the support cuffs 26, 27. Exterior support strap(s) 28 would then be wrapped around the arm over the support sleeve as needed to thoroughly secure and bind all perilimb medical equipment. A water absorbent dam 60 would then be clipped to the upper arm just above the support cuff 25. The adsorbent material 62 and elastic closure strap 64 would then be wrapped around the upper arm and secured using the hook and loop attachments 66, 67 on the elastic closure strap 64. A second water adsorbent dam 50 or cuff would then be pulled over the hand and positioned on the wrist over support cuff 24. Finally, the waterproof sleeve 90 would be drawn over the hand and arm, covering the absorbent dams 50, 60 and support sleeve 20. Adjustable sealing bands 92, 93 would then be tightened around the waterproof sleeve, gathering the waterproof material tightly around the upper arm and wrist, forming waterproof seals with the underlying skin. The excess waterproof material above the upper arm seal may be folded down so as not to catch water.

Figure 13:
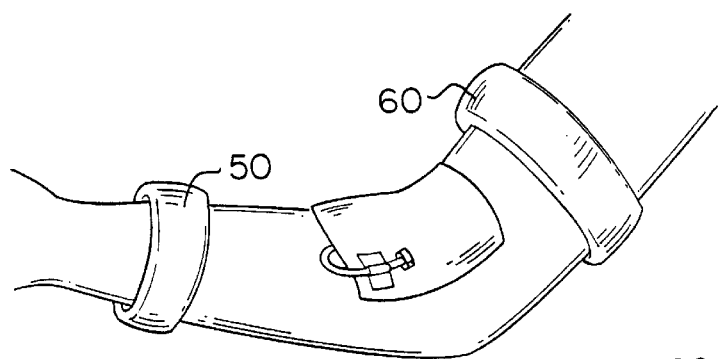
FIG. 13 is the same view as FIG. 12 showing the first step in applying the preferred embodiment.
Figure 14:
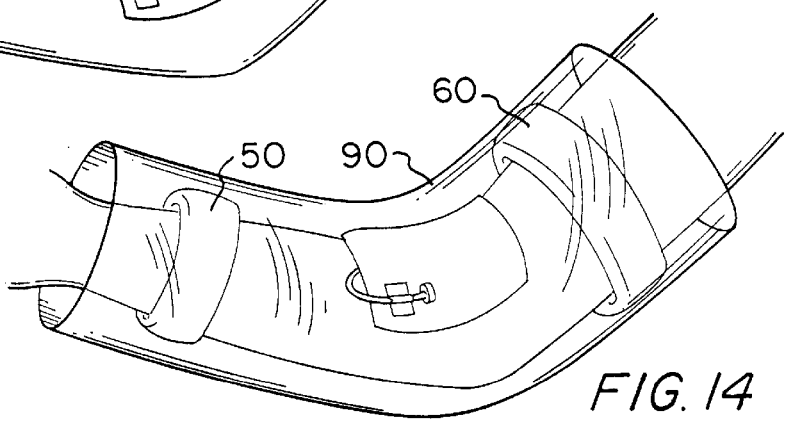
FIG. 14 is the same view as FIG. 12 showing the second step in applying the preferred embodiment.
Figure 15:
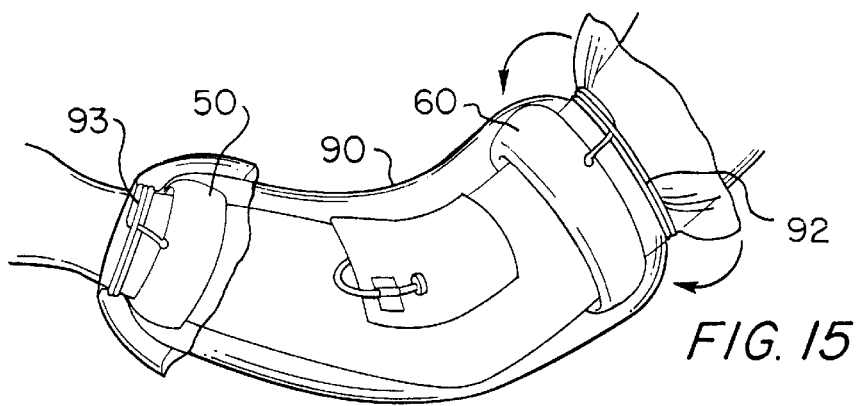
FIG. 15 is the same view as FIG. 12 showing the completed application of the preferred embodiment.

Note that though the invention is shown with a support sleeve 20 inside a waterproof sleeve 90, the waterproof sleeve 90 and absorbent dams 50, 60 may be used without the support sleeve 20, and visa versa. Refer to FIGS. 12–15 for clarification. PICC-line 120 is covered by bandage 121. The water absorbent dams 50, 60 and waterproof sleeve 90 and adjustable elastic sealing bands 92, 93 keep the bandage 121 dry during a shower. Additionally note that though two different types of water absorbent dams 50, 60 are shown, one at the top, and the other at the bottom of the waterproof sleeve 90, these need not necessarily be of different designs. Finally note that though the invention is shown installed over the midarm on an arm, it can also be used on legs. It may also be designed to completely cover an arm and hand, or a leg and foot.

Although the present invention has been described with reference to a preferred embodiments, numerous modifications and variations can be made and still the results will come within the spirit and scope of this invention. No limitation with respect to the specific embodiments disclosed herein is intended or should be inferred.

What is claimed is:

1. A limb covering comprising:
   a waterproof sleeve means functioning to loosely encircle a portion of a limb having a medical appliance;
   a first water absorbent dam means functioning to encircle an upper portion of the limb underneath an upper portion of the waterproof sleeve means;
   a second water absorbent dam means functioning to encircle a lower portion of the limb underneath a lower portion of the waterproof sleeve means;
   a first sealing means functioning to encircle the upper portion of the waterproof sleeve means above the first water absorbent dam; and
   a second sealing means functioning to encircle the lower portion of the waterproof sleeve means below the second water absorbent dam means, whereby water is prevented from entering under the waterproof sleeve means by the formation of a double barrier at each end.

2. The apparatus of claim 1, wherein said waterproof sleeve means further comprises a thin, limp walled, waterproof plastic.

3. The apparatus of claim 1, wherein said first and second water absorbent dam means each further comprise a single continuous piece of stretchable cotton ribbing.

4. The apparatus of claim 1, wherein said first waterproof dam further comprises:
   a "C" shaped resilient stay; and
   a means for closing said dam around the limb functioning to keep out water, wherein said first water absorbent dam has a first and a second end, said first end has a pocket engaging said "C" shaped stay, and said second end is adapted to wrap at least once around the limb.

5. The apparatus of claim 4, wherein said means for closing said dam around the limb further comprises a hook and loop fastener.

6. The apparatus of claim 1, wherein said first sealing means further comprises an elastic band.

7. A waterproof covering and medical appliance support, comprising:
   a waterproof sleeve adapted to encircle a portion of a limb;
   said sleeve having at least one opening to receive the limb;
   means for double sealing the opening functioning to keep out water;
   said means for double sealing the opening further comprising a water absorbent dam and a closing means; and
   a medical appliance support sleeve having a mounting means underneath said waterproof sleeve.

8. The apparatus of claim 7, wherein the waterproof sleeve further comprises a thin, limp walled plastic.

9. The apparatus of claim 7, wherein said water absorbent dam further comprises a continuous piece of stretchable cotton ribbing.

10. The apparatus of claim 7, wherein said closing means further comprises an elastic band.

11. The apparatus of claim 7, wherein said medical appliance support sleeve further comprises an inner surface having a pocket for removable insertion of said medical appliance.

12. The apparatus of claim 7, wherein said medical appliance support sleeve further comprises a stretchable material.

13. The apparatus of claim 7, wherein said waterproof sleeve further comprises a second opening adapted to provide for the encirclement of a mid-portion of the limb, and a second means for double sealing the second opening functioning to keep out water.

14. A limb covering comprising:
   a waterproof sleeve adapted to encircle a portion of a limb;
   said waterproof sleeve having an opening at one end;
   a double barrier waterproof seal at the one end; and
   said double barrier waterproof seal further comprising a water absorbent dam under the waterproof sleeve and adapted to encircle the limb, and a closing band adapted to encircle the waterproof sleeve.

* * * * *